US006387321B1

(12) United States Patent
McGill

(10) Patent No.: US 6,387,321 B1
(45) Date of Patent: May 14, 2002

(54) METHOD FOR CONTROLLING TOILET ODOR

(76) Inventor: Eric McGill, 6480 Ducketts La., Elkridge, MD (US) 21075

( * ) Notice: Subject to any disclaimer, the term of this patent is extended or adjusted under 35 U.S.C. 154(b) by 0 days.

(21) Appl. No.: 09/517,962

(22) Filed: Mar. 3, 2000

Related U.S. Application Data

(62) Division of application No. 09/268,155, filed on Mar. 15, 1999, now Pat. No. 6,054,423.

(51) Int. Cl.[7] ........................... A61L 9/00; C11D 77/04

(52) U.S. Cl. ........................................... 422/5; 510/191

(58) Field of Search ................................ 510/191, 367; 422/5

(56) References Cited

U.S. PATENT DOCUMENTS

| | | | | |
|---|---|---|---|---|
| 1,078,918 A | | 11/1913 | Gruter | |
| 3,762,875 A | | 10/1973 | Burmeister | 21/60.5 A |
| 4,200,606 A | | 4/1980 | Kitko | 422/37 |
| 4,229,408 A | * | 10/1980 | Bennett et al. | 422/5 |
| 4,416,786 A | | 11/1983 | Knorre et al. | 210/746 |
| 4,578,207 A | | 3/1986 | Holdt et al. | 253/134 |
| 4,579,677 A | | 4/1986 | Hooper et al. | 252/95 |
| 4,780,216 A | | 10/1988 | Wojtowicz | 210/756 |
| 5,071,622 A | | 12/1991 | Dunson | 422/5 |
| 5,137,687 A | | 8/1992 | Dunson | 422/5 |
| 5,445,741 A | | 8/1995 | Dilla et al. | 210/631 |
| 5,575,945 A | | 11/1996 | Perlman | 252/176 |
| 5,602,090 A | | 2/1997 | Melikyan et al. | 510/372 |
| 5,610,126 A | | 3/1997 | Barford et al. | 510/191 |
| 5,709,872 A | | 1/1998 | Van Rees | 424/420 |
| 5,753,602 A | | 5/1998 | Hung et al. | 510/192 |
| 5,910,473 A | | 6/1999 | Alfano et al. | 510/191 |
| 5,958,334 A | * | 9/1999 | Haddon | 422/5 |
| 6,015,536 A | * | 1/2000 | Lokkesmoe et al. | 423/210 |

FOREIGN PATENT DOCUMENTS

| | | |
|---|---|---|
| DE | 262 139 A3 | 1/1987 |
| FR | 438417 | 7/1914 |
| FR | 438417 | 10/1922 |

OTHER PUBLICATIONS

Waldrip et. al, "Elimination of odor at six major wastewater treatment plants," Journal WPCF, vol. 57, No. 10, (Oct. 1985) pp. 1027–1032.

* cited by examiner

*Primary Examiner*—Yogendra Gupta
*Assistant Examiner*—John M. Petruncio
(74) *Attorney, Agent, or Firm*—Steven J. Hultquist

(57) ABSTRACT

The present invention provides a process for controlling toilet odors by use of compositions comprising a hypochlorite compound and a hydrogen peroxide compound. The compositions are useful for preventing, reducing and/or eliminating the odor emitting capacity of human or animal excrement in an aqueous solution.

15 Claims, 1 Drawing Sheet

METHOD FOR CONTROLLING TOILET ODOR

RELATED APPLICATION

The present application is a divisional of U.S. patent application Ser. No. 09/268,155 filed Mar. 15, 1999, now U.S. Pat. No. 6,054,423.

BACKGROUND OF THE INVENTION

1. Field of the Invention

The present invention relates generally to compositions and methods for preventing and controlling toilet odors. More specifically, the invention relates to compositions comprising a hypochlorite compound and a hydrogen peroxide compound and methods for preventing, reducing and/or eliminating the odor emitting capacity of fecal material and human waste in toilet water. Comprising such compositions to the water.

2. Description of the Related Art

The odor produced in toilets during the excretion of fecal material from the human body is often offensive and disturbing to the excreter or other persons nearby. For the excreter, the toilet odor can also be a source of embarrassment The source of offense and embarrassment is the odor which is produced in toilet environments during the momentary period when excreted fecal material or other human waste is introduced into and allowed to remain in the toilet water before being flushed. The offensive odors diffuse through the toilet water and into the atmosphere of the toilet environment.

This present invention provides compositions comprising a hypochlorite compound and a hydrogen peroxide compound for preventing, reducing and/or eliminating toilet odor comprising adding to the toilet water an effective amount of such composition. Addition of the compositions transforms the toilet water into a solution that chemically attacks the odor-emitting agents present in the fecal material or other human waste.

The use of hypochlorite compounds and hydrogen peroxide compounds individually to sanitize waste water, swimming water and drinking water is known. It is also known to use hypochlorite compounds and hydrogen peroxide successively and/or simultaneously to sanitize and deodorize waste water, swimming water and drinking water. However, there remains a need in the art for compositions and methods for sanitizing and deodorizing toilet water. U.S. Pat. Nos. 4,578,207 and 5,753,602 reveal the use of chlorine containing compounds to make cake like tablets for sustained release of the active ingredients to sanitize and deodorize toilets. However, there is a need in the art for compositions which provide a vigorous, instantaneous chemical attack on toilet odors.

U.S. Pat. No. 4,200,606 discloses the use of a hypochlorite sanitizing agent that aims to sanitize the toilet bowl with each flush. These preparations are placed in the astern or water holding tank and treat the water that is present there. However, there is a need in the art for compositions which can be used to prepare a vigorous odor-eliminating toilet water solution for receiving fecal materials and rapidly eliminating or reducing the odor thereof.

The hypochlorite ion reacts rapidly with hydrogen peroxide in water. The odor-preventing, reducing and/or eliminating capability of the composition of this invention is effective up to 9–12 minutes (the critical time period). There is therefore a need for a means for providing an effective odor-controlling composition using these compounds that remain stable during storage, yet retain the ability to react when added to toilet water. The compositions and methods taught in the prior art do not provide a combination of ingredients that are appropriate or that will remain active long enough to vigorously attack the odor emitting agents during the critical time period. They also do not provide compositions or methods that can ensure bat an effective concentration of these ingredients will be present in the toilet bowl during the critical time period.

Furthermore, while the compositions and methods of the prior art focus mainly on cleaning the bowl and preventing odor emitting agents from accumulating over a long period of time, there is a need for compositions which can prepare the toilet water to prevent, eliminate or significantly reduce the odor that is produced during bowel excretion. Finally, many of the toilets used in industrial and office settings, hospitals, dormitories, ballparks and portable toilets do not have water holding tanks to place these kind of sanitizers. The methods mentioned in the art do not address the sanitizing, odor controlling need that exists where these toilets are used.

An object of this present invention is to provide a method for preventing, significantly reducing and/or eliminating odors emitted when human waste are introduced into all toilets types. This object is achieved by the liquid, tabletted, powdered, granulated and/or encapsulated preparations of the present invention. Placement of the active ingredients and/or compositions comprising the active ingredients into the toilet bowl immediately prior to use, ensures the prevention, reduction and/or elimination of toilet odor. Addition of the active ingredients to toilet water converts the water into a solution that reduces the odor emitting capacity of human waste in the toilet water.

Another object of this invention is to provide a method for instantly sanitizing toilets.

SUMMARY OF THE INVENTION

This invention provides an odor reducing/elimination composition and methods for introducing such composition into toilet water to effect odor prevention, reduction and/or elimination. The composition includes an effective amount of a hypochlorite solution or compound, and a hydrogen peroxide solution or compound. In one aspect, the compositions also include a fragrance and/or perfume.

The method of the invention generally comprises dispensing the composition (e.g., dropping, pouring or otherwise dispensing into the toilet water prior to bowel excretion.

The chemical composition is supplied in various forms, such as in liquid form, powder form, granule form, tablet form, or capsule form. The chemical composition can also be packaged in a small bag-like container (baggette) that preferably separates the active ingredients. The small bag like containers can be treated with any of the fragrances to avoid mixing the fragrances with the other components. The compositions can be contained and dispensed from plastic or metal containers. The chemical composition can also be dispensed into the toilet immediately prior to use from a dispensing apparatus.

This invention can be used in all toilets. This includes toilets found in all settings with and without water holding tanks. The invention may also be used to temporarily sanitize and control odor in waste water systems.

The term "hydrogen peroxide compound" is used herein to refer to hydrogen peroxide per se or any compound or group of compounds capable of providing hydrogen peroxide upon contact with water or with the other ingredients of the compositions of the present invention.

The term "hypochlorite compound" is used herein to refer to hypochlorite per se or any compound or group of compounds capable of providing hypochlorite upon contact with water or with the other ingredients of the compositions of the present invention.

The term "active ingredients" is used herein to refer to hydrogen peroxide compounds and hypochlorite compounds.

DETAILED DESCRIPTION OF THE INVENTION

This present invention provides novel compositions and methods for vigorously attacking the odors caused by human waste, such as fecal material and other bodily discharges in such a manner that the sharp, offensive and often embarrassing odors associated with toilet bowl use are prevented, significantly reduced and/or eliminated. The chemical composition generally comprises a hydrogen peroxide compound and a hypochlorite compound, a fragrance and/or perfume, and various inactive ingredients.

Preferred hypochlorite compounds have the general formula X(OCl)α, where X is selected from the group consisting of calcium, lithium, potassium and sodium, and α is a number from 1 to 2. Because it is readily available as a solid, calcium hypochlorite is preferred when preparing a solid embodiment of the invention. Calcium hypochlorite has the additional advantage that it is less toxic and cheaper than lithium hypochlorite. Sodium hypochlorite is preferred when preparing a liquid embodiment of the invention. All are available from Fluka Chemfika-BioChemika, Buchs, Switzerland and Acros Organics, Pittsburgh, Pa. The hydrogen peroxide compounds are represented by the formula $Y\text{-}H_2O_2$, where Y represents an adduct compound selected from the group consisting of sodium percarbonate and carbamide-peroxide. These compounds are available from Fluka Chemika-BioChemika, Buchs, Switzerland.

Any known fragrance and/or perfume can be employed in the compositions of the present invention. Fragrances and/or perfumes that are insoluble and/or less dense than toilet water can be used to limit their interaction with the primary reaction if desired. Because of environmental concerns, insoluble fragrances should be used in very small quantities. Fragrances and/or perfumes commonly employed by cleaning and sanitizing industry are preferred. Preferred fragrances include Allspice, Balsam, Bouquet, Christmas Pine, Citronella, Citrus Fresh, Citrus 7305 & 7309, Clean & Fresh, Cove, Deodorizer, Earth & Sea, Eucalyptus, Evergreen, any of the Floral series (3788, 9451,8444, 4788, 9436 & 9940), Fresh & Clean 7902 & 8003, Fresh Outdoors. Gardenia, any of the Herbal series (8916, 4555, 8144 & 3719), Honeysuckle, Jasmin, any of the Lemon series ( 6001, 6039, 8136, 9413 & 9414), any of the Odor Mask series (5211, 6794, 7851, 8833, 8836, 8838, 8839, 8899 & 8899 w/s), any of the Pine series (9434, 8329 & 9435), Rose 9297 & 9298, Sandalwood, Sea Breeze, Spring Clean and Spring Rain; all are available from The Good Scents Company, Atlanta, Ga. The Pine, Citronella and Citrus fragrances are most preferred. Other fragrances and/or perfumes useful in the practice of the invention include the fragrances commonly used in the household and industrial cleaning and sanitizing industry. Such fragrances are described in the catalog *Flavors & Fragrances,* the disclosure of which is incorporated herein by reference in its entirety and are available from the Aldrich Chemical Company, Inc., Milwaukee, Wis. Those of particular interest are Alpha Pinene, Alpha Terpineol, Beta Pinene, Cedar Leaf, Citral, Citronellal W230707-7, Coumarin, Diethylphthalate, Eucolyptol, Eugenol, Heptyl isobutyrate, trans-2-Hexen-1ol, Isobornyl and 3,5,5-Trimehtylhexanal.

The compositions of the present invention may also comprise various inactive ingredients known in the art for preparing tablets, capsules, cleaning solutions and the like. Further, various ingredients may be added to lower the pH to a range that is tolerable to human skin if necessary.

Each of the active components has some ability to either mask, or reduce odors. When used independently, the ability of each to prevent, reduce and/or eliminate toilet bowl odor is insignificant However, the inventor has surprisingly discovered that when used together, the active ingredients act synergistically to achieve the goal of preventing, significantly reducing and/or eliminating toilet bowl odor. The inventor has further discovered that when the solid components are used to provide the active ingredients, the advantages of the liquid formulation are lost, due to the relatively low solubility rate of the hypochlorite compound. This difficulty is overcome by using sodium percarbonate as the hydrogen peroxide compound, which, rapidly releases hydrogen peroxide in water in the presence of a hypochlorite containing compound. The hydrogen peroxide then reacts with the hypochlorite compound, causing the hypochlorite ions to be released at a much faster rate. This reaction alone provides most of the ability of this invention to prevent, significantly reduce and/or eliminate toilet bowl odor. The perfume and/or fragrance adds to the effectiveness of the odor-preventing, reducing and/or eliminating ability, and also serves to mask the bleach smell that is produced when the hypochlorite ions are liberated. The reaction of hydrogen peroxide with the hypochlorite ions also reduces the bleach smell.

When preparing the solid embodiments of the invention, hydrogen peroxide urea adduct and sodium percarbonate are the preferred active ingredients.

A preferred liquid composition liquid of the present invention can be prepared from 3%, 30% or 35% hydrogen peroxide solutions available from Fluka Chemika-BioChemika, Buchs, Switzerland and Acros Organics, Pittsburgh, Pa.

In a preferred embodiment, the liquid preparation of the invention can be packaged as two or three discrete liquid or solid units as follows:

1. A first unit comprising 100–150 ml of a 5.25% sodium hypochlorite solution;
2. A second unit comprising 50–150 ml of a 3% hydrogen peroxide solution, or 10–15 ml of a 30% or 35% hydrogen peroxide solution; and
3. A optional third unit comprising 10–15 ml of a concentrated fragrance such as pine oil The fragrance may optionally be combined with one of the first two units.

The present invention also comprises a dispensing apparatus for dispensing the liquid preparations of the active ingredient into the toilet water. Any dispensing apparatus can be used which will prevent the hypochlorite solution from mixing with the hydrogen peroxide solution before they reach the toilet bowl. The dispensing apparatus can, for example, be attached to any solid surface proximal to the toilet with a tube or tubes from the solution containers positioned in the toilet to allow the solutions to flow into the toilet. The dispensing apparatus can be operated by the user by a button or any other means that would dispense the appropriate volume of liquids into the toilet immediately prior to use. For example, a conventional liquid-dispensing means may be configured to automatically dispense an odor-reducing, -preventing or -eliminating amount of the active ingredients when a user sits on the seat of the toilet A preferred solid preparation of this invention can contain the following:

1. a first unit comprising 2–7 g of calcium hypochlorite while the preferred range is 4–6 g;
2. a second unit comprising 500 mg–7 g of sodium percarbonate, while the preferred range is 4–6 g; and
3. an optional third unit comprising 100 mg–5 g of any fragrance or perfume.

In addition to the ingredients listed above, the tablet preparation can contain any of a variety of excipients (binders, disintergrants, glidants, lubricants and anti-adherents) taught in the art, preferably oxipients which permit the tablet to quickly dissolve upon contact with water, i.e., effervescent tablet formulation. Also, excipients that are known to provide a sustained release of tabletted compositions can be used to prepare the tablet preparations of the present invention. Preferred excipients include, for example, food acids like citric acid, malic acid, or add salts; due to their pH lowering ability. The tablets are optionally layered and/or partitioned to prevent mixing of the hypochlorite containing compound.

The active ingredients may also be encapsulated using materials and methods that are generally known in the art.

The tablets or capsules of the present invention may be packaged in any type of material that prevents water and excessive moisture from reacting with the preparation, e.g., foil.

Separation of the hypochlorite containing compound from the hydrogen peroxide containing compound is not strictly necessary in the solid preparations, but is expected to improve storage life of the solid preparations.

DESCRIPTION OF DRAWINGS

In one aspect, the formulation is in powder or granulated form and is packaged in a container, such as a plastic container, with holes in the top to allow the user to pour the components; like those used for the household cleaner Comet. The container can contain any kind of lid that could be opened and closed in such a way that prevents moisture from entering. This container has an outer wall 101*a,* a bottom wall 101*b* and a top wall 101*c* which together enclose a total interior volume. The interior volume is divided by at least one separating wall 102 into two sub-interior volumes 103*a* and 103*b* for containing the active ingredients, i.e., the hypochlorite compound 105 and the hydrogen peroxide compound 106. The container also has a top having a plurality of holes 104 for dispensing the granules or powders. In a preferred method, the container has a partition which prevents the hypochlorite compound from mixing with the hydrogen peroxide compound if long term mixing of the components presents a problem. The fragrance and/or perfume can be mixed with either compound or with both compounds.

The powder or granulated form of the active ingredients may also be packaged in a bagette constructed from a permeable, filter paper-like material; e.g., like the material that is used in tea bags. The material selected must permit the dissolved components to leave the packaging to react in the toilet water. These bagettes can be of any size or shape, and can be constructed as necessary to separate the hypochlorite compound from the hydrogen compound. When present, the fragrance and/or perfume can be mixed with either compound, or with both compounds, or the container material can be treated with the fragrance and/or perfume prior to packaging. The powdered or granulated preparations of the invention can also be packaged in foil, plastic or any type of material that would prevent water and excessive moisture from reacting with the preparation.

Figure 1:
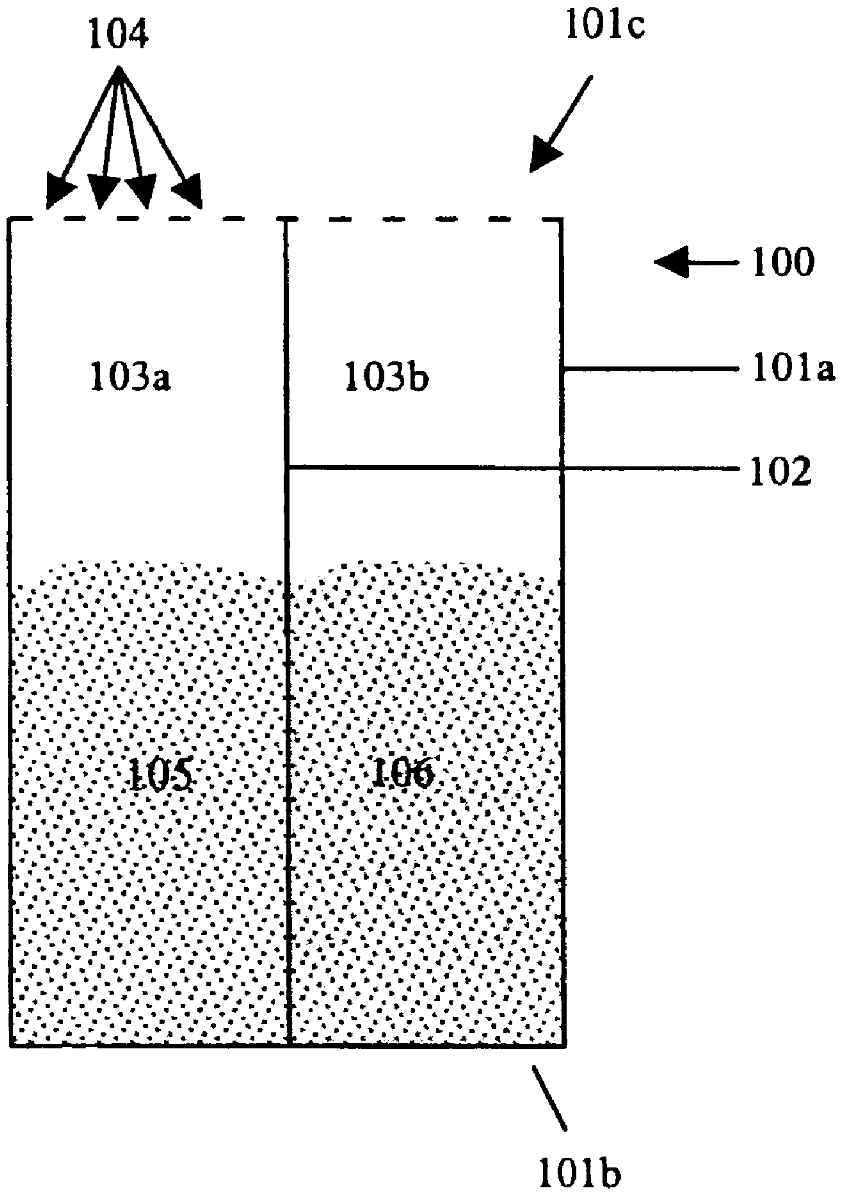

The present invention also provides methods for using the active ingredients for deordorizing toilet water. A preferred method is as follows:

1. the active ingredients are brought, either simultaneously or consecutively, into association with toilet water prior to introducing any solid waste into the toilet bowl;
2. the user preferably allows 5 seconds for the liquid composition to disperse in the toilet bowl, or 5–20 seconds for the tabletted preparations to dissolve and disperse in the toilet bowl water, or 5–15 seconds for the powdered and/or granulated preparations to dissolve and disperse in the toilet bowl water;
3. human waste products are introduced to the toilet water; and
4. the user flushes the toilet contents immediately after the completion of waste excretion.

EXAMPLES

To determine the effect of this invention on toilet odor production, compositions of 3% hydrogen peroxide solutions with 5.25% sodium hypochlorite solutions and/or sodium percarbonate with calcium hypochlorite were added to toilet bowls. Fifteen percent pine oil solutions were also used with some compositions. The primary control compositions included a 15% pine oil solution alone. Other compositions that were tested include a 3% hydrogen peroxide solution alone, a 5.25% sodium hypochlorite solution alone, sodium percarbonate alone, calcium hypochlorite alone, a 3% hydrogen peroxide solution with a 15% pine oil solution, a 5.25% sodium hypochlorite solution with a 15% pine oil solution, calcium hypochlorite with a 15% pine oil solution, and sodium percarbonate with a 15% pine oil solution.

Testers were instructed to do the following: pour the solutions separately into the toilet bowl immediately prior to bowel excretion, excrete bowel contents as usual, and then flush the toilet. They were also instructed to make observations by smelling to detect the extent of bowel odor and bleach odor. One observation was made during the bowel excretion process and two observations were made during the 1–3 minute period immediately after completing the entire process. The first after-use observation was made before leaving the bathroom or toilet area, and the last after use observation was made after leaving for 1–2 minutes and returning. Testers were also instructed to find a nonuser to make one observation during the 1–3 minute after use period (whenever possible). The test scale for each observation was 0–10 with 0 indicating no odor and 10 indicating an extremely bad odor.

2.1 Example I Liquid Composition Without Fragrance

| | Toilet odor observation | | | Bleach odor observation | | | Percentage |
|---|---|---|---|---|---|---|---|
| Composition | 1 | 2 | 3 | 1 | 2 | 3 | reduction |
| (a) 100 ml 3% $H_2O_2$ + 100 ml 5% NaClO | 2.0 | 1.9 | 1.7 | 3.8 | 4.1 | 3.7 | 76.7% |
| (b) 100 ml 3% $H_2O_2$ + 100 ml $H_2O$ | 8.2 | 8.2 | 8.1 | 0 | 0 | 0 | 13.7% |
| (c) 100 ml 5% NaClO + 100 ml $H_2O$ | 7.8 | 7.9 | 7.7 | 6.8 | 6.3 | 6.1 | 17.3% |
| (d) No composition | 9.5 | 9.6 | 9.5 | 0 | 0 | 0 | |

Odor reduction percentage = Control Avg. (d) − Composition Avg. (a, b or c)

2.2 Example II Liquid Composition With Fragrance

| | Toilet odor observation | | | Bleach odor observation | | | Percentage |
|---|---|---|---|---|---|---|---|
| Composition | 1 | 2 | 3 | 1 | 2 | 3 | reduction |
| (a) 100 ml 3% $H_2O_2$ + 100 ml 5% NaClO + 1 ml 15% pine oil | 1.7 | 1.6 | 1.4 | 2.2 | 2.4 | 2.5 | 76.4% |
| (b) 100 ml 3% $H_2O_2$ + 1 ml 15% pine oil | 7.7 | 7.6 | 7.6 | 0 | 0 | 0 | 15.7% |
| (c) 100 ml 5% NaClO + 1 ml 15% pine oil | 7.2 | 7.3 | 7.3 | 5.4 | 5.3 | 5.1 | 19.4% |
| (d) 1 ml 15% pine oil | 9.2 | 9.3 | 9.1 | 0 | 0 | 0 | |

Odor reduction percentage = Control Avg. (d) − Composition Avg. (a, b or c)

2.3 Example III Powder Composition Without Fragrance

| | Toilet odor observation | | | Bleach odor observation | | | Percentage |
|---|---|---|---|---|---|---|---|
| Composition | 1 | 2 | 3 | 1 | 2 | 3 | reduction |
| (a) 5 g NasCO3.1.5$H_2O_2$ + 5 g Ca(OCl)s | 1.8 | 1.6 | 1.3 | 2.4 | 2.9 | 2.6 | 79.7% |
| (b) 5 g NasCO3.1.5$H_2O_2$ | 8.3 | 8.2 | 8.1 | 0 | 0 | 0 | 13.3% |
| (c) 5 g Ca(OCl)s | 8.7 | 8.6 | 8.6 | 0.7 | 0.9 | 0.6 | 9.0% |
| (d) No composition | 9.6 | 9.6 | 9.4 | 0 | 0 | 0 | |

Odor reduction percentage = Control Avg. (d) − Composition Avg. (a, b or c)

2.4 Example IV Powder Composition With Fragrance

| | Toilet odor observation | | | Bleach odor observation | | | Percentage |
|---|---|---|---|---|---|---|---|
| Composition | 1 | 2 | 3 | 1 | 2 | 3 | reduction |
| (a) 5 g $NasCO_3$.1.5$H_2O_2$ + 5 g Ca(OCl)s + 1 ml 15% pine oil | 1.6 | 1.4 | 1.3 | 1.6 | 1.9 | 1.6 | 80.4% |
| (b) 5 g $NasCO_3$.1.5$H_2O_2$ + 1 ml 15% pine oil | 8.1 | 8.2 | 7.9 | 0 | 0 | 0 | 14.0% |
| (c) 5 g Ca(OCl)s + 1 ml 15% pine oil | 8.2 | 8.0 | 8.0 | 0.4 | 0.5 | 0.4 | 14.0% |
| (d) 1 ml 15% pine oil | 9.5 | 9.6 | 9.3 | 0 | 0 | 0 | |

Odor reduction percentage = Control Avg. (d) − Composition Avg. (a, b or c)

I claim:

1. A process for reducing odor from excreted waste material that is excreted into a vessel containing water, the process comprising adding to said water an odor-reducing amount of:

(a) a hypochlorite compound; and (b) a hydrogen peroxide compound, so that (a) and (b) are contemporaneously present with one another in said water.

2. The process of claim 1 further comprising adding to the water a perfume or scent-producing component.

3. The process of claim 1 wherein the hypochlorite compound and the hydrogen peroxide compound are added simultaneously.

4. The process of claim 1 wherein the hypochlorite compound and the hydrogen peroxide compound are added consecutively.

5. The process of claim 1 wherein the hypochlorite compound is provided in solution and is added separately from the hydrogen peroxide compound.

6. The process of claim 1 wherein the hypochlorite compound is provided as a solid.

7. The process of claim 1 wherein the hydrogen peroxide compound is provided in solution and is added separately from the hypochlorite compound.

8. The process of claim 1 wherein the hydrogen peroxide compound is provided as a solid.

9. The process of claim 1 wherein the hypochlorite compound and hydrogen peroxide compound are provided in a single solid unit and compounds (a) and (b) are added simultaneously.

10. The process of claim 1 wherein the hypochlorite compound has the formula:

$$XOCl_{\alpha}$$

where X is selected from the group consisting of calcium, lithium, potassium and sodium, and $\alpha$ is 1 or 2.

11. The process of claim 1 wherein the hydrogen peroxide compound has the formula:

$$Y—H_2O_2$$

where Y is an adduct compound.

12. The process of claim 1 wherein the hydrogen peroxide compound is sodium percarbonate or carbamide peroxide.

13. The process of claim 1 wherein compounds (a) and (b) are added simultaneously.

14. The process of claim 1 wherein said water comprises toilet water.

15. The process of claim 1 wherein the hypochlorite compound and the hydrogen peroxide compound are added to the toilet water 5 to 30 seconds prior to defecation.

* * * * *